US005112604A

United States Patent [19]

Beaurline et al.

[11] Patent Number: 5,112,604

[45] Date of Patent: May 12, 1992

[54] ORAL SUSPENSION FORMULATION

[75] Inventors: Joseph M. Beaurline, North St. Paul; Stephen M. Berge; Robert K. Schultz, both of Shoreview, all of Minn.

[73] Assignee: Riker Laboratories, Inc., St. Paul, Minn.

[21] Appl. No.: 411,903

[22] Filed: Sep. 1, 1989

[51] Int. Cl.[5] ........................................ A61K 31/79

[52] U.S. Cl. ........................................ 424/490; 424/71; 424/440; 424/494; 514/263; 514/772.2; 514/772.3; 514/772.7; 514/781

[58] Field of Search ........................ 424/440, 80, 71, 78

[56] References Cited

U.S. PATENT DOCUMENTS 4,940,588 7/1990 Sparks et al. ........................ 424/490
4,988,679 1/1991 Chavkin et al. ........................ 514/53
5,008,117 4/1991 Calanchi ........................ 424/494

FOREIGN PATENT DOCUMENTS 2166651B 11/1988 United Kingdom .

*Primary Examiner*—Thurman K. Page
*Assistant Examiner*—D. Gabrielle Phelan
*Attorney, Agent, or Firm*—Gary L. Griswold; Walter N. Kirn; Doulgas E. Reedich

[57] ABSTRACT

An aqueous suspension for oral administration of a drug, which suspension is storage stable for a prolonged period and maintains the drug in suspension during such period.

28 Claims, No Drawings

ORAL SUSPENSION FORMULATION

BACKGROUND OF THE INVENTION

1. Field of the Invention

This invention pertains to pharmaceutical liquid suspension formulations suitable for oral administration In another aspect, it pertains to sustained release suspensions. In yet another aspect, this invention pertains to theophylline formulations.

2. Description of Related Art

Theophylline is an antiasthmatic drug with a narrow therapeutic window. It is available in a number of different dosage forms including conventional tablets, sustained release tablets, elixirs and suspensions. The currently available suspensions settle to the bottom of the container upon standing for several days. If the container is not shaken adequately, the contents will not resuspend in a uniform fashion and the amount of theophylline present per dose will vary.

European Patent Application 0,101,418 (Kallstrand et al.) discloses what is said to be a controlled release pharmaceutical mixture which masks bad taste and increases stability of an active substance, characterized in that an encapsulated active substance is combined with a substance controlling the release of the active substance. The release-controlling substance is a carbohydrate or a carbohydrate-related material and microencapsulated theophylline is among the enumerated actives.

UK Pat. No. GB 2166651B discloses a suspension of pharmasomes containing theophylline. The suspension vehicle consists of (by weight): 85.3% 70% sorbitol solution, 0.7% Avicel RC 591, 0.3% potassium sorbate, 2.7% of a solution containing titanium dioxide 25% in 70% sorbitol, 0.01% simethicone 10% emulsion, 10.8% glycerine, 0.3% citric acid and 0.04% sodium lauryl sulphate.

SUMMARY OF THE INVENTION

This invention provides an aqueous pharmaceutical suspension for oral administration which suspension, based on the total weight of the suspension, comprises from about 0.1 to 15 percent by weight of a particulate medicament with an average particle size of less than about 150 μm; about 0.02 percent to about 5 percent by weight of a pharmaceutically acceptable wetting agent; about 0.02 to about 0.10 percent by weight of a hydrocolloid gum; about 0.2 to about 2.0 percent by weight of colloidal silicon dioxide; about 0.1 to 0.3 percent by weight of an antifoaming agent; a carbohydrate which is dissolved in the suspension; and water; the suspension being further characterized in that the medicament remains suspended uniformly for a period of at least about 90 days when tested according to the Test Method.

Due to the presence of the hydrocolloid gum and the colloidal silicon dioxide, the suspension of the invention maintains the medicament in suspension for a prolonged period of time without shaking. The amount of medicament therefore remains uniform from dose to dose during this period. Dosage uniformity is of particular importance when the medicament comprises a drug with a narrow therapeutic window such as theophylline.

In a preferred embodiment, the medicament is in the form of a controlled release polymeric particle comprising a drug, which drug is dispersed throughout the polymeric particle.

DETAILED DESCRIPTION OF THE INVENTION

A suspension of the invention contains from about 0.02 percent to about 5 percent, preferably from about 0.1 to about 0.8 percent, by weight of a pharmaceutically acceptable wetting agent based on the total weight of the suspension. If the wetting agent is a solid, it is soluble in the suspending medium. The choice of wetting agent can influence the in vitro release rate of a controlled-release particulate medicament. Preferred wetting agents include sorbitan monolaurate, polysorbate 21, sodium lauryl sulfate and sorbitan monolaurate in combination with polysorbate 20. The most preferred wetting agent is a 4:1 sorbitan monolaurate:polysorbate 20 combination.

A hydrocolloid gum in combination with colloidal silicon dioxide serves as a suspending agent. The gum is present in an amount of from about 0.02 to about 0.10 percent, preferably 0.04 to about 0.08 percent by weight based on the total weight of the suspension. The gum can be, e.g., guar gum, locust bean gum, gum tragacanth, xanthan gum, and the like. Xanthan gum is preferred. The colloidal silicon dioxide is present in an amount of from about 0.2 to 2.0 percent, preferably 0.2 to about 0.8 percent, and more preferably 0.4 to about 0.7 percent by weight based on the total weight of the suspension. Colloidal silicon dioxide is available from DeGussa under the trade designation Aerosil TM or under the trade designation Cab-O-Sil TM. A preferred colloidal silicon dioxide is Aerosil TM 200 brand colloidal silicon dioxide.

A suspension of the invention also comprises from about 0.1 to about 0.3 percent by weight based on the total weight of the suspension of a conventional antifoaming agent which is preferably simethicone emulsion.

The suspension further comprises a carbohydrate and water. As is conventional, for a given volume of water used, the carbohydrate is preferably present in the suspension in an amount which binds substantially all of the free water in the suspension so that the solubility of the drug, whether in particulate form, microencapsulated, or dispersed throughout a polymeric particle, is minimized as a result of having minimized the solvent activity of the water contained in the suspension. Suitable suspending media include conventional syrups used in pharmaceutical suspensions. Preferred suspending media are selected from the group consisting of 70% sorbitol in water solution (w/v), simple syrup, and mixtures thereof. Simple syrup and 70% sorbitol in water solution (w/v) are described, e.g., in U.S.P. XXII, the disclosure of which is incorporated by reference herein. The most preferred suspending medium is a 1:1 mixture of 70% sorbitol:simple syrup.

A suspension of the invention can optionally further comprise from about 0.1 to about 1 percent by weight based on the total weight of the suspension of a pharmaceutically acceptable preservative. Preferred preservatives include sodium benzoate, methyl paraben, propyl paraben, potassium sorbate, potassium sorbate in combination with citric acid, and mixtures thereof. Commercially available Simple Syrup, N.F. contains a suitable preservative, e.g., 0.1% sodium benzoate.

A suspension of the invention can optionally further comprise from about 3 to about 5 percent by weight based on the total weight of the suspension of a pharmaceutically acceptable dispersing aid such as propylene glycol or preferably glycerin.

A suspension of the invention can optionally further comprise a pharmaceutically acceptable flavoring agent.

A suspension of the invention can also optionally further comprise a pharmaceutically acceptable dye.

A suspension of the invention comprises from about 0.1 to about 15 percent, preferably from about 1 to 10 percent, and most preferably from about 2 to about 7 percent, by weight based on the total weight of the suspension of a particulate medicament with an average particle size of less than about 150 μm, preferably between about 50 μm and about 125 μm.

The medicament can be employed as is in particulate form.

Alternatively, the particulate drug can be microencapsulated using, for example, a conventional material such as hydroxypropyl cellulose, beeswax, hydrogenated castor oil, hydrogenated vegetable oil, hydrogenated tallow, glyceryl stearate, glyceryl palmito stearate, or the like.

Still alternatively and preferably, the medicament is in the form of an active ingredient dispersed throughout a polymeric particle. Preferred polymeric particles contain an active ingredient (e.g., a drug) and optionally an excipient in intimate admixture with at least one non-toxic polymer, with the active ingredient and the excipient, if present, substantially uniformly distributed throughout the polymeric particle. The particles have an average size of between 0.1 and 125 μm and have a predetermined release of active ingredient when the dissolution thereof is measured according to the Paddle Method of U.S. Pharmacopoeia XXII. The dissolution rate of the particles is substantially proportional to the square root of time.

Non-toxic polymers useful in preparing polymeric particles are alkyl celluloses, hydroxyalkyl celluloses, cellulose ethers, cellulose esters, nitro celluloses, polymers of acrylic and methacrylic acids and esters thereof, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes and polyurethanes and copolymers thereof.

Most drugs can be prepared in suitable form and are thus suitable for use in suspensions of the invention. The drug can, for example, be an antiallergic, antiinflammatory, antihistamine, antitussive, antibiotic, antiarrhythmic, vasodilator, psychotropic, analgesic, anticonvulsant, bronchodilator, antiasthmatic, antibacterial, antihypertensive or a mixture thereof. A particularly preferred drug is theophylline.

The optional excipient used in association with the drug can affect the release of the drug. For example, the excipient can be a surfactant that facilitates the transport of water into a polymeric particle. It can be an organic acid that facilitates the dissolution of active ingredients that are poorly soluble in alkaline media. It can be a base that facilitates the dissolution of active ingredients that are poorly soluble in acidic media.

A stable, uniform sustained-release theophylline suspension of the invention is suitable for oral administration and, based on the total weight of the suspension, comprises from about 0.1 to about 15 percent by weight of polymeric particles comprising theophylline.

The most preferred non-toxic polymer for the preparation of polymeric particles containing theophylline is cellulose acetate butyrate. Suitable particles comprising theophylline and methods of preparation therefor are disclosed in UK Patent GB 2166651B, the disclosure of which is incorporated herein by reference. Example 1 of said patent discloses a method by which suitable particles may be made. Other methods for preparing suitable particles are also disclosed in said patent.

The amount of drug in the particles can be varied as desired, e.g., to affect the amount of particles required for an effective dose or to affect the release profile of the particles. Preferred theophylline suspensions of the invention contain from about 100 to about 300 mg of theophylline per 5 mL of suspension.

Suspensions of the invention can be prepared by first blending together the suspension medium, the hydrocolloid gum, the colloidal silicon dioxide, the preservative, if any, and the dispersing aid, if any. The polymeric particles, wetting agent and antifoaming agent can then be combined to give a concentrate. This concentrate can then be combined with the previously prepared blend. The suspensions of the invention can be prepared using conventional vacuum or non-vacuum liquid processors. They are preferably prepared in liquid vacuum processors such as the VME TM brand mixer (available from Fryma Inc.) and the Unimix TM brand mixer (available from Haagen & Rinao Mischtechnik GmbH). It is particularly desirable to use liquid vacuum processors when the suspensions being prepared contain a low level of suspending agent, i.e., less than 0.04% hydrocolloid gum and/or less than 0.4 % colloidal silicon dioxide.

Prior to being used in the suspensions of the examples below, the polymeric particles to be used were analyzed for particle size, theophylline content and dissolution rate. The theophylline content was measured using conventional high-pressure liquid chromatography methodology. The dissolution rate was measured according to the Paddle Method of U.S. Pharmacopoeia XXII.

The polymeric particles used to prepare the suspensions of Examples 1, 2 and 3 below had the following characteristics: the polymer used was cellulose butyrate acetate, 99.8% passed through a 125 μm screen, they contained 532 mg of theophylline per gram of polymeric particles, and the dissolution rate was 36.2% at 1 hour, 72.1% at 4 hours and 98.3 % at 12 hours.

Test Method for Suspension Uniformity

A suspension of the invention is capable of maintaining the medicament in suspension so that the top and bottom medicament concentrations are within ±10% when maintained at 40° C. for at least about 90 days, preferably at least about 120 days, and most preferably at least about 180 days without shaking at any point during the test period.

Top and bottom medicament concentrations are determined according to the following procedure.

This test is done using a 225 mL bottle which contains 200 mL volume of suspension. A 5 or 10 mL polypropylene syringe with a 12 or 14 gauge 6 inch needle is used and the needle is marked such that it will penetrate the suspension ½ inch. The needle is placed ½ inch into the top of the suspension and 5 mL is drawn. The needle is removed from the syringe, the plunger is pulled back to allow for headspace, the syringe is shaken until well mixed, and 3 mL of the sample is discarded. The end of the syringe is capped. For bottom sampling, another 5 or 10 mL polypropylene syringe with a 12 or 14 gauge, 6 inch needle is used. The needle is placed all the way to the bottom of the bottle and 5 mL is drawn. The needle is removed, the plunger is pulled back to allow for headspace, the syringe is shaken until well mixed and 3 mL of the sample is discarded. The end of syringe is capped. A known weight from the 2 mL of the sample is analyzed for drug content.

This Test Method for Suspension Uniformity is referred to as the "Test Method" in the instant specification and claims.

The following examples are provided to illustrate the invention and are not intended to be limiting thereof.

EXAMPLE 1

Simple syrup (29,763.11 g), 29,763.11 g of 70% sorbitol and 130.0 g of potassium sorbate were placed in a Unimix TM brand mixer then blended and homogenized under vacuum until all of the potassium sorbate was dissolved. The citric acid (227.5 g) was added and blended. The glycerin (2,600.0 g) and 39.0 g of xanthan gum were placed in a stainless steel beaker and mixed with a spatula until homogeneous. The glycerin/xanthan gum dispersion was added to the blend in the mixer and blended and homogenized under vacuum. Aerosil TM 200 brand colloidal silicon dioxide was added and then blended and homogenized under vacuum. Theophylline polymeric particles (1,794.0 g), 26.0 g of sorbitan monolaurate, 104.0 g polysorbate 20, 130.0 g simethicone emulsion, 32.5 g of cherry flavor, and about 400 g of the blend from the mixer were placed in a stainless steel beaker and blended to give a paste. This paste and 0.78 g of Red 40 FD&C were added to the remainder of the blend in the mixer and blended under vacuum until homogenous. The resulting suspension contained 100 mg of theophylline per 5 ml of suspension and had the composition shown in Table 1. Dissolution data are shown in Table 2.

TABLE 1

| Ingredient (% w/w) | Example 1 | Example 2 | Example 3 |
|---|---|---|---|
| Simple syrup | 45.79 | 45.76 | 44.42 |
| 70% Sorbitol solution | 45.79 | 45.76 | 44.42 |
| Potassium sorbate | 0.20 | 0.20 | 0.20 |
| Citric acid | 0.35 | 0.35 | 0.35 |
| Xanthan gum | 0.06 | 0.06 | 0.06 |
| Glycerin | 4.00 | 4.00 | 4.00 |
| Silicon dioxide | 0.60 | 0.60 | 0.60 |
| Red #40 FD&C | 0.0012 | 0.0012 | — |
| Sorbitan monolaurate | 0.04 | 0.04 | 0.04 |
| Polysorbate 20 | 0.16 | 0.16 | 0.16 |
| Simethicone emulsion | 0.20 | 0.20 | 0.20 |
| Theophylline Polymeric Particles | 2.76 | 2.76 | 5.52 |
| Cherry flavor | 0.05 | — | — |
| Strawberry flavor | — | 0.10 | — |
| Mint flavor | — | — | 0.025 |

TABLE 2

| Time (min) | 30 | 60 | 120 | 240 | 360 | 720 | 1200 |
|---|---|---|---|---|---|---|---|
| | % Released | | | | | | |
| Example 1 | 28.5 | 38.5 | 50.9 | 65.0 | 74.3 | 89.3 | 96.2 |
| Example 2 | 30.9 | 40.9 | 53.0 | 67.2 | 76.8 | 92.0 | 98.2 |

EXAMPLE 2

Using the general method of Example 1, a suspension containing 100 mg of theophylline per 5 ml of suspension and having the composition shown in Table 1 was prepared. Dissolution data are shown in Table 2 above.

EXAMPLE 3

Using the general method of Example 1, a suspension containing 200 mg of theophylline per 5 ml of suspension and having the composition shown in Table 1 above was prepared. The general method of this Example was repeated except that 44.4075 weight percent of each of the simple syrup and sorbitol solution were used and 0.05 weight percent of cherry flavor was substituted for the mint flavor.

EXAMPLE 4

Simple syrup (2843.7 g) and 70% sorbitol in water solution (2843.7 g) were blended in a glass beaker. Citric acid (21.0 g) was added and the mixture was stirred until the citric acid was dissolved. Potassium sorbate (12.0 g) was added and the mixture was blended for about 10 minutes. A dispersion of xanthan gum (3.6 g) and glycerin (240 g) was prepared, added to the mixture, and blended for about 15 minutes in a Gifford-Wood homogenizer. Colloidal silicon dioxide (36.0 g of Aerosil TM 200 brand colloidal silicon dioxide) was added and homogenization was continued for about 15 minutes to provide a vehicle. A concentrate was prepared by mixing salicylsalicylic acid powder with a particle size of less than 125 μm (14.0 g), simethicone emulsion (0.97 g), vehicle as prepared above (50 g), and an 80/20 (w/w) blend of Tween TM 20 brand polysorbate 20 and Span TM 20 brand sorbitan monolaurate (0.97 g) in a mortar. The concentrate was then blended into the vehicle as prepared above (417 g) and homogenized to afford the suspension of Example 4 with the composition shown in Table 3.

TABLE 3

| Ingredient | % w/w |
|---|---|
| Salicylsalicylic acid | 2.90 |
| Ethyl cellulose-coated salicylsalicylic acid | — |
| Silicon dioxide | 0.58 |
| Xanthan gum | 0.06 |
| potassium sorbate | 0.19 |
| simethicone emulsion | 0.20 |
| glycerin (99%) | 3.87 |
| citric acid | 0.34 |
| 70% sorbitol | 45.83 |
| simple syrup | 45.83 |
| Span/Tween | 0.20 |

What is claimed is:

1. An aqueous pharmaceutical suspension for oral administration which suspension, based on the total weight of the suspension, comprises from about 0.1 to 15 percent by weight of a particulate medicament with an average particle size of less than about 150 μm; about 0.02 percent to about 5 percent by weight of a pharmaceutically acceptable wetting agent; about 0.02 to about 0.10 percent by weight of a hydrocolloid gum; about 0.2 to about 2.0 percent by weight of colloidal silicon dioxide; about 0.1 to 0.3 percent by weight of an antifoaming agent; a carbohydrate which is dissolved in the suspension; and water; the suspension being further characterized in that the medicament remains suspended uniformly for a period of at least about 90 days when tested according to the Test Method for suspension uniformity.

2. A suspension according to claim 1, wherein the hydrocolloid gum is xanthan gum.

3. A suspension according to claim 1, wherein the colloidal silicon dioxide is present in an amount of between about 0.2 to about 0.8 percent by weight based on the total weight of the suspension.

4. A suspension according to claim 1, wherein the particulate medicament has an average particle size of between about 50 μm and about 125 μm.

5. A suspension according to claim 1, wherein the medicament is present in an amount of from about 1 to about 10 percent by weight based on the total weight of the suspension.

6. A suspension according to claim 5, wherein the medicament is present in an amount of from about 2 to about 7 percent by weight based on the total weight of the suspension.

7. A suspension according to claim 1, wherein the medicament is in the form of a microencapsulated drug.

8. A suspension according to claim 1, wherein the medicament is in the form of controlled release polymeric particles comprising a drug and optionally an excipient in intimate admixture with at least one non-toxic polymer, with the drug and the excipient, if present, substantially uniformly distributed throughout the polymeric particle, and which particles have a predetermined release of the drug when the dissolution rate thereof is measured according to the Paddle Method of U.S. Pharmacopoeia XXII.

9. A suspension according to claim 8, wherein the non-toxic polymer is selected from the group consisting of an alkyl cellulose, a hydroxyalkyl cellulose, a cellulose ether, a cellulose ester, a nitro cellulose, a polymer of acrylic and methacrylic acids and esters thereof, a polyamide, a polycarbonate, a polyalkylene, a polyalkylene glycol, a polyalkylene oxide, a polyalkylene terephthalate, a polyvinyl alcohol, a polyvinyl ether, a polyvinyl ester, a polyvinyl halide, a polyvinylpyrrolidone, a polyglycolide, a polysiloxane, and a polyurethane.

10. A suspension according to claim 9, wherein the non-toxic polymer is cellulose acetate butyrate.

11. A suspension according to claim 1, wherein the medicament comprises a drug selected from the group consisting of an antiallergic, an antiinflammatory, an antihistamine, an antitussive, an antibiotic, an antiarrhythmic, a vasodilator, a psychotropic, an analgesic, an anticonvulsant, a bronchdilator, an antiasthmatic, an antibacterial, an antihypertensive, and a mixture of any two or more of the foregoing thereof.

12. A suspension according to claim 11, wherein the drug is theophylline.

13. A suspension according to claim 1, wherein the carbohydrate is present in an amount that minimizes the solvent activity of the water contained in the suspension.

14. A suspension according to claim 7, wherein the carbohydrate is present in an amount that minimizes the solvent activity of the water contained in the suspension.

15. A suspension according to claim 8, wherein carbohydrate is present in an amount that minimizes the solvent activity of the water contained in the suspension.

16. A suspension according to claim 1, further comprising from about 0.1 to 1 percent by weight based on the total weight of the suspension of a pharmaceutically acceptable preservative.

17. A suspension according to claim 16, wherein the preservative is selected from the group consisting of sodium benzoate, methyl paraben, propyl paraben, potassium sorbate, potassium sorbate in combination with citric acid and mixtures thereof.

18. A suspension according to claim 1, further comprising from about 3 to about 5 percent by weight based on the total weight of the suspension of a pharmaceutically acceptable dispersing aid.

19. A suspension according to claim 18, wherein the dispersing aid is glycerin.

20. A suspension according to claim 1, further comprising a pharmaceutically acceptable flavoring agent.

21. A suspension according to claim 1, further comprising a pharmaceutically acceptable dye.

22. A suspension according to claim 1, wherein the wetting agent is selected from the group consisting of sorbitan monolaurate, polysorbate 21, sodium lauryl sulfate, and sorbitan monolaurate in combination with polysorbate 20.

23. A suspension according to claim 22, wherein the wetting agent is present in an amount of from about 0.1 to about 0.8 percent by weight based on the total weight of the suspension.

24. A suspension according to claim 1, wherein the antifoaming agent is simethicone emulsion.

25. A suspension according to claim 1, wherein the gum is present in an amount of from about 0.04 to about 0.08 percent by weight based on the total weight of the suspension.

26. A suspension according to claim 1, wherein the colloidal silicon dioxide is present in an amount of from about 0.4 to about 0.7 percent by weight based on the total weight of the suspension.

27. A suspension according to claim 1, wherein the medicament remains suspended uniformly for a period of at least about 90 days when tested according to the said Test Method.

28. A suspension according to claim 1, wherein the medicament remains suspended uniformly for a period of at least about 180 days when tested according to the said Test Method.

* * * * *